United States Patent [19]
Guigan

[11] Patent Number: 4,876,203
[45] Date of Patent: * Oct. 24, 1989

[54] METHOD OF PERFORMING MEDICAL ANALYSIS ON A LIQUID SAMPLE USING AT LEAST ONE DRY REAGENT, AND APPARATUS FOR THE METHOD

[76] Inventor: Jean Guigan, 9, rue Jean Mermoz, 75008 Paris, France

[*] Notice: The portion of the term of this patent subsequent to May 10, 2005 has been disclaimed.

[21] Appl. No.: 790,021

[22] Filed: Oct. 22, 1985

[30] Foreign Application Priority Data

Oct. 26, 1984 [FR] France ............................ 84 16448

[51] Int. Cl.⁴ .......................................... G01N 21/07
[52] U.S. Cl. ...................................... 436/45; 422/64; 422/72; 422/102; 436/174; 436/180
[58] Field of Search ............... 436/174, 179, 180, 45; 422/72, 64, 102

[56] References Cited

U.S. PATENT DOCUMENTS

| | | | |
|---|---|---|---|
| 3,211,368 | 10/1965 | Shanley | 494/17 |
| 3,814,582 | 6/1974 | Rohrbaugh et al. | 422/64 |
| 3,951,608 | 4/1976 | Trod | 422/64 |
| 4,469,793 | 9/1984 | Guigan | 422/102 |
| 4,632,908 | 12/1986 | Schultz | 422/72 |
| 4,673,653 | 6/1987 | Guigan | 422/64 |

FOREIGN PATENT DOCUMENTS

2503866 10/1982 France.

OTHER PUBLICATIONS

Shultz, Clin. Chem., vol. 31, No. 9, 1985.

*Primary Examiner*—Michael S. Marcus
*Attorney, Agent, or Firm*—Sughrue, Mion, Zinn, Macpeak, and Seas

[57] ABSTRACT

A method of medically analyzing a liquid sample using a single-piece container (1) made of plastic. The container is divided into a sample storage chamber (4), a calibrated cell (6), a diluent storage chamber (30), and reaction chambers (40, 50, 60). Various centrifuging operations are performed to cause the sample and the diluent to pass successively through the various reaction chambers.

6 Claims, 5 Drawing Sheets

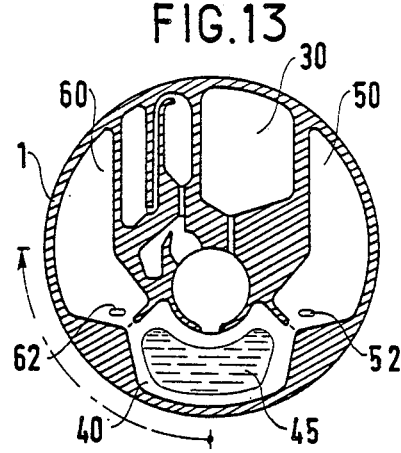
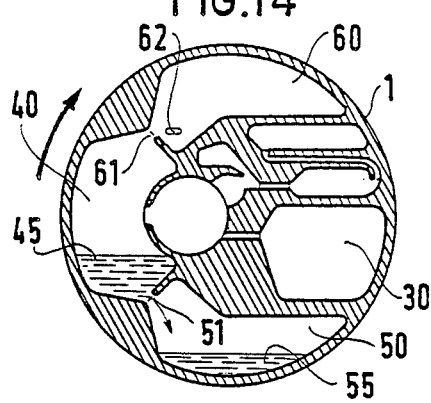
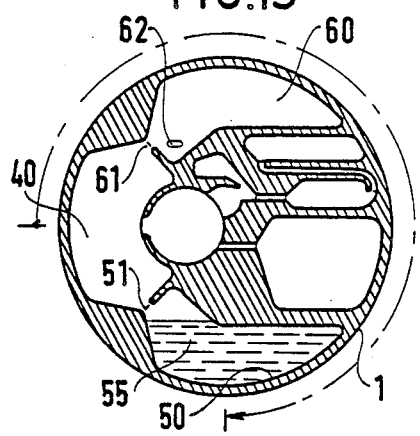
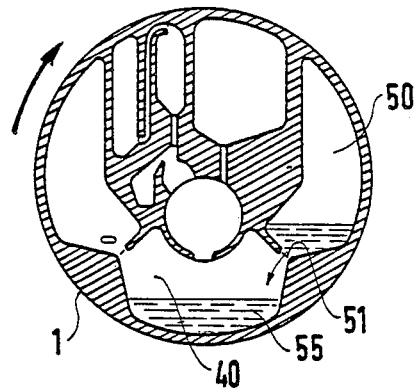
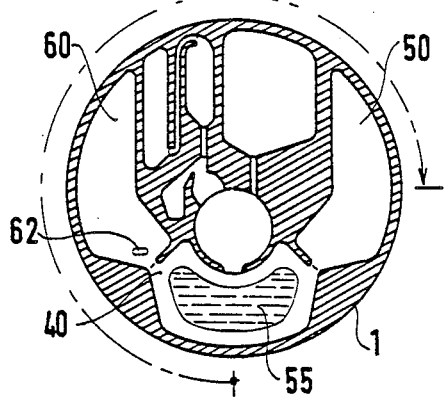
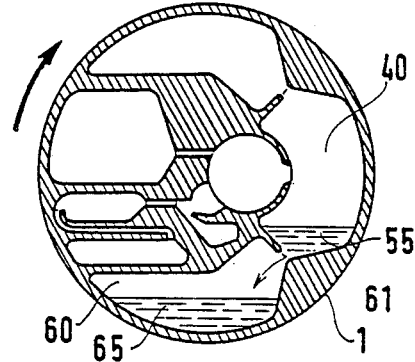

METHOD OF PERFORMING MEDICAL ANALYSIS ON A LIQUID SAMPLE USING AT LEAST ONE DRY REAGENT, AND APPARATUS FOR THE METHOD

The present invention relates to a method for performing medical analysis on a liquid sample using at least one dry reagent, and to apparatus for performing the method.

One aim of the present invention is to provide a method of analyzing a very small quantity of liquid sample, e.g. a few microliters. This is particularly advantageous when performing medical analysis since it then becomes possible to avoid taking samples of blood from patients by means of a syringe since a few drops of blood collected from the end of a finger will suffice.

Another aim of the invention is to provide a method capable of performing most of the medical analyses currently required (there are about 300 such analyses).

A final aim of the invention is to provide a method which is cheap and which is simple for an operator who merely has to make use of stored containers which contain dry reagents and a diluent.

SUMMARY OF THE INVENTION

The present invention provides a method of performing medical analysis on a liquid sample using at least one dry reagent together with a diluent, the method uses a container having internal compartments disposed to provide:

a storage chamber for said liquid sample and connected via a capillary duct to one end of a calibrated cell whose other end is connected via a capillary duct to an overflow chamber;

a storage chamber for said liquid diluent;

a pouring chamber connected via respective capillary ducts to said calibrated cell and to said diluent storage chamber, and also communicating with a first reaction chamber suitable for containing a dry reagent; and two reaction chambers suitable for containing dry reagents situated on either side of said first reaction chamber, and communicating therewith via capillary ducts having different orientations.

Said container is closed by a lid which is fitted both with a sample storing receptacle communicating directly with said sample storage chamber and situated thereabove, and with a removable stopper which penetrates into said pouring chamber to close the ends of said capillary ducts leading thereto. Means are provided to position said container on the turntable of a centrifuge in several different predetermined positions which differ from one another by rotating the container about its own axis relative to the turntable and through a given angle.

According to the method, a liquid diluent is initially available in said diluent storage chamber and the dry reagents are available in respective ones of said reaction chambers.

Said sample is inserted into the sample storing receptacle and then flows under gravity into said sample storage chamber, and said stopper is removed. The container is placed on said centrifuge turntable in order to perform a plurality of successive centrifuging operations, with the angular position of the container being chosen on each occasion from among said predetermined positions as a function of the orientation of the capillary duct concerned relative to the direction of centrifugal force in such a manner as to cause said sample to pass successively from said sample storage chamber into said calibrated cell, then into said pouring chamber, and then into said first reaction chamber, and subsequently into each of the other reaction chambers.

In a particularly advantageous embodiment, said predetermined positions of the container are separated from one another by rotations of about 90° and about 180°, and correspond substantially to the angles between said capillary ducts.

The present invention also provides apparatus for performing the above-defined method. The apparatus comprises a flat cylindrical container made of plastics material and having a diameter of about three centimeters, which container is compartmented internally so as to provide:

a first storage chamber for said liquid sample connected via a capillary duct to one end of a calibrated cell whose other end is connected via a capillary duct to an overflow chamber;

a storage chamber for said liquid diluent;

a pouring chamber connected via respective capillary ducts to said calibrated cell and to said diluent storage chamber, and also communicating with a first reaction chamber suitable for containing a dry reagent; and two reaction chambers suitable for containing dry reagents and situated on either side of said first reaction chamber and communicating therewith via capillary ducts having different orientations.

The said container is a single molded part. The capillary ducts have diameters of about 2 tenths of a millimeter.

The container is closed by a lid made of plastics material and provided with a sample storage receptacle communicating directly with said sample storage chamber and situated thereabove. The lid also has a chimney situated above said pouring chamber in order to receive a stopper suitable for closing all the orifices opening into said pouring chamber. The chimney, the receptacle and the lid are made from a single piece of molded plastics material.

In a particularly advantageous embodiment, the capillary ducts causing said calibrated cell and said diluent storage chamber to communicate with the pouring chamber are parallel to each other. The capillary ducts causing the reaction chambers to communicate with one another are diametrically opposed about the pouring chamber and are at a non-zero angle relative to the two above-specified capillary ducts.

The present invention also provides the above apparatus when the diluent storage chamber contains a few microliters of diluent and when each of said reaction chambers contains a dry reagent in the form of a pencil lead shaped pellet having a length of a few millimeters.

BRIEF DESCRIPTION OF THE DRAWINGS

An embodiment of the invention is described by way of example with reference to the accompanying drawings, in which:

FIGS. 7 to 18 are diagrams showing various positions of the container containing its sample and its reagents during the various stages of the method in accordance with the invention.

MORE DETAILED DESCRIPTION

FIGS. 1 to 6 show a container 1 made of plastics material and generally in the form of a flat cylinder which is closed by a lid 2, likewise made of plastics material. By way of example, the container may have a diameter of about three centimeters.

Figure 1:
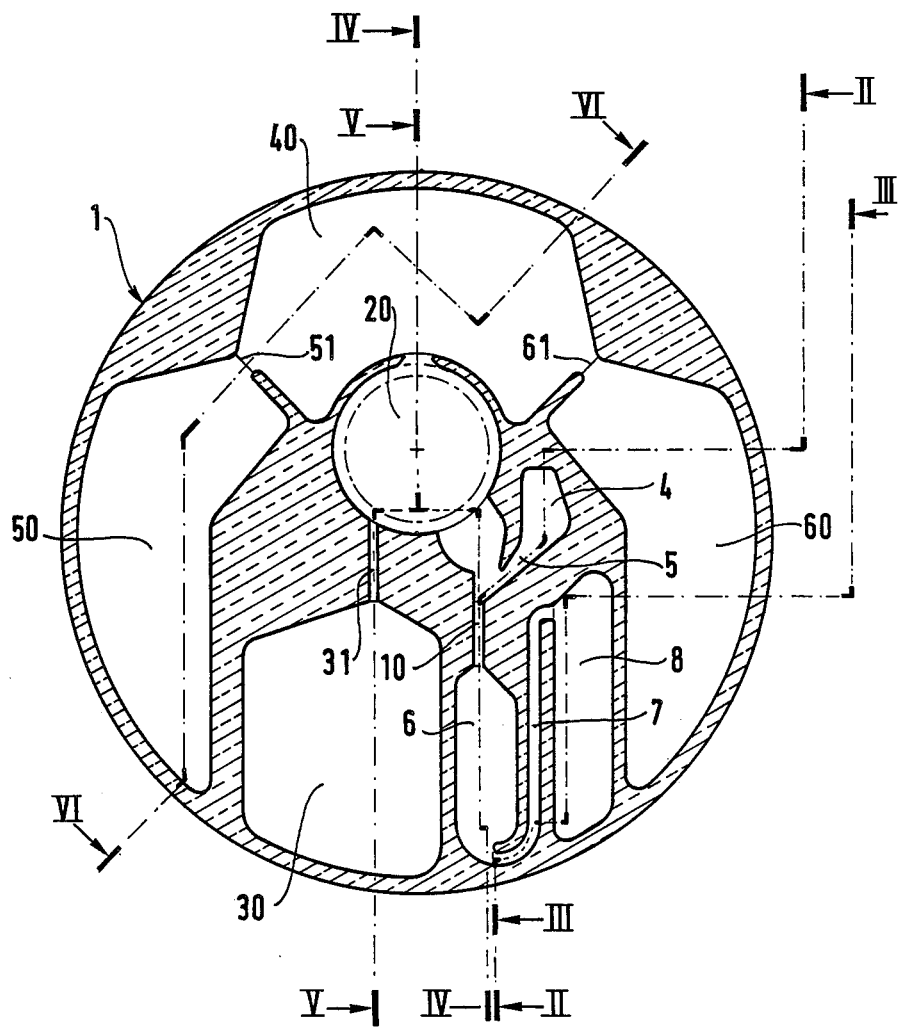
FIG. 1 is a top plan view of a container with its lid removed.
Figure 2:
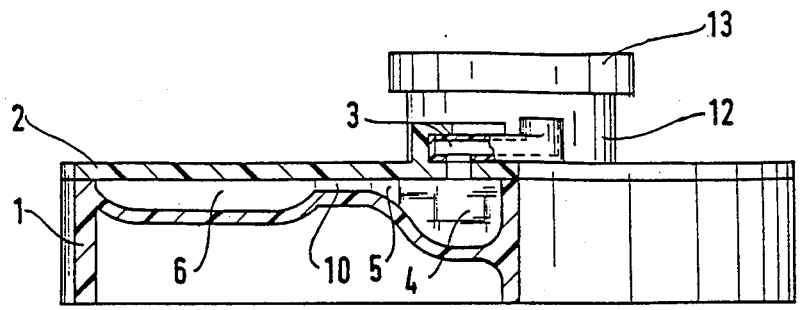
FIGS. 2 to 6 are section views through the container on section lines II—II to VI—VI respectively of FIG. 1.
Figure 3:
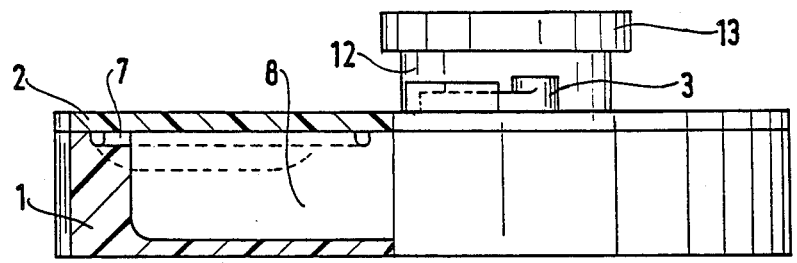

FIGS. 1 and 2 show that the top portion of the lid 2 bears a storage receptacle 3 for a liquid sample in direct communication with a sample storage chamber 4 inside the container 1.

Figure 4:
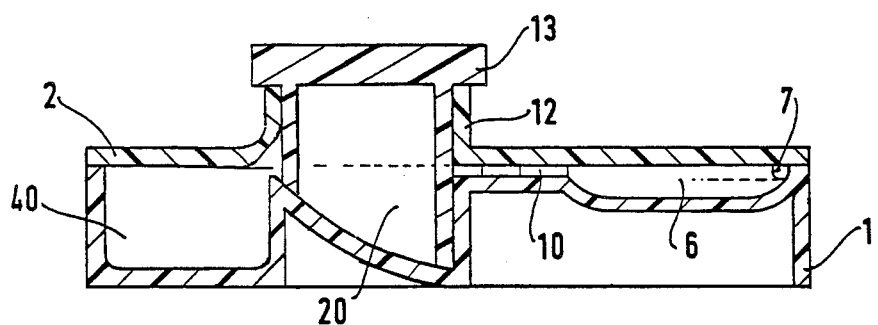

The storage chamber 4 is connected via a capillary duct 5 to a calibrated cell 6 which communicates via a capillary duct 7 with an overflow chamber 8 (see FIG. 3) and via a capillary duct 10 with a pouring chamber 20 (see FIG. 4). The pouring chamber communicates with a reaction chamber 40 suitable for containing a dry reagent.

Figure 5:
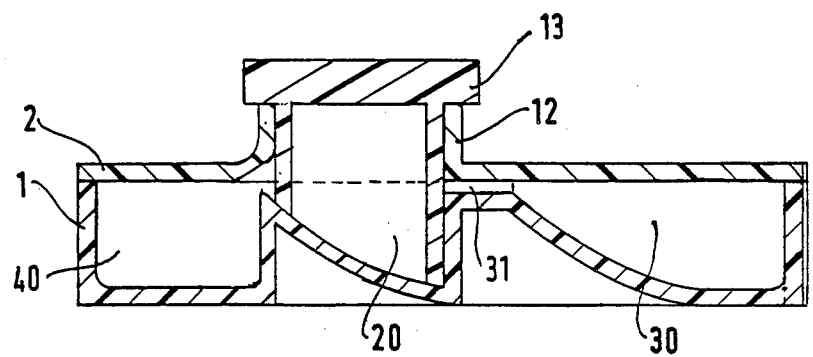
Figure 6:
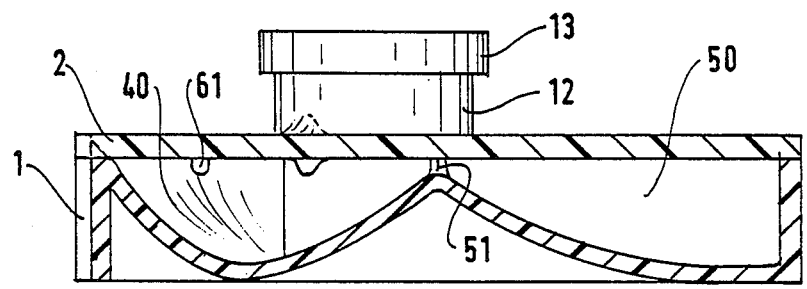

The container 1 further includes a diluent storage chamber 30 in communication with the pouring chamber 20 via a capillary duct 31 (see FIG. 5). It may be observed here that the capillary ducts 10 and 31 are substantially parallel to each other. Two other reaction chambers are referenced 50 and 60 and are suitable for containing respective dry reagents (see FIG. 6). These chambers are situated on either side of the reaction chamber 40 and are in communication therewith via two capillary ducts 51 and 61 which are at an angle to each other and at an angle to the capillary ducts 10 and 31.

Above the pouring chamber 20 the lid 2 bears a chimney 12 suitable for receiving a stopper 13. Throughout the period when the container is stored together with its reagents, the stopper 13 serves above all to close the orifice of the capillary duct 31 leading to the pouring chamber 20.

FIGS. 7 to 18 are plan views of the apparatus shown in FIGS. 1 to 6 during implementation of the method in accordance with the invention.

Figure 7:
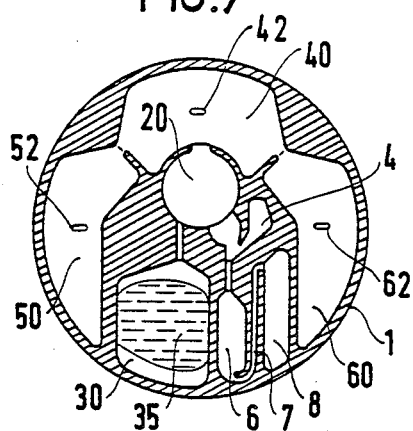
Figure 8:
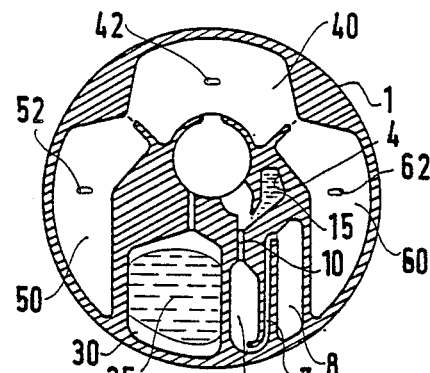
Figure 9:
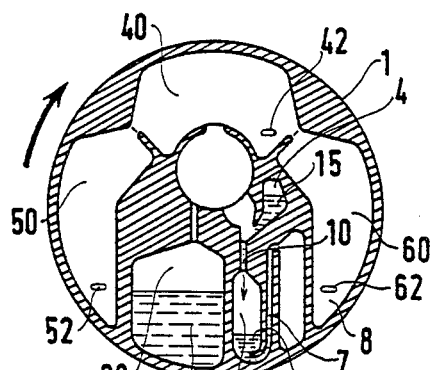
Figure 10:
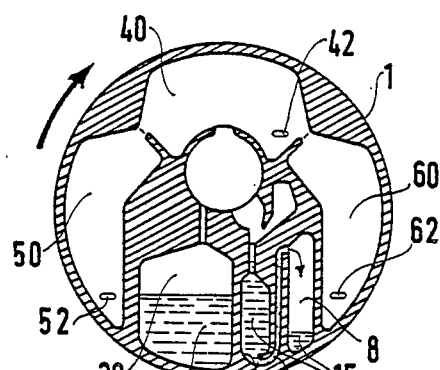
Figure 11:
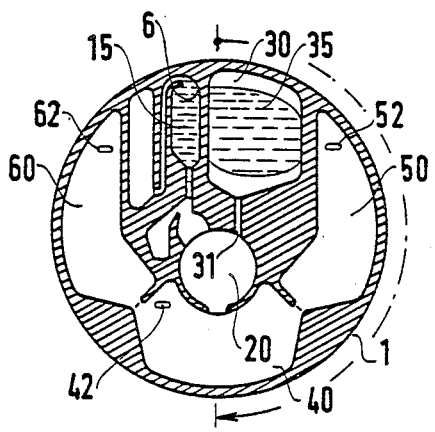

FIG. 7 shows an initial stage during which the chambers 40, 50, and 60 of the container 1 contain respective dry reagents 42, 52, and 52. The chamber 30 contains a liquid diluent 35.

The container 1 is then placed on the turntable of a centrifuge. It will readily be understood that at least a dozen such containers may be placed in a circle on such a turntable. The center of rotation of the turntable is situated in such a manner that the end of the cell 6 which is connected to the capillary duct 7 lies further from the center of rotation than does the end of the cell 6 which corresponds to the capillary duct 10. The direction of centrifugal force is substantially parallel to the capillary ducts 10 and 31.

At this moment the stopper 13 is removed and a drop comprising a few microliters of sample 15 is inserted into the receptacle 3. The sample 15 penetrates into the storage chamber 4 (see FIG. 8).

A first centrifuging operation is then performed and an intermediate stage (FIG. 9) and the final stage (FIG. 10) thereof are shown in the drawings. The dry reagents and the diluent remain stored in their respective chambers, while the sample 15 passes into the calibrated cell 6 and the capillary duct 7. Once the calibrated cell 6 is full of sample 15, excess sample ends up in the overflow chamber 8.

The container is then rotated through 180° about its own axis (see FIG. 11) so that the capillary ducts 10 and 31 are still parallel to the direction of centrifugal force.

Figure 12:
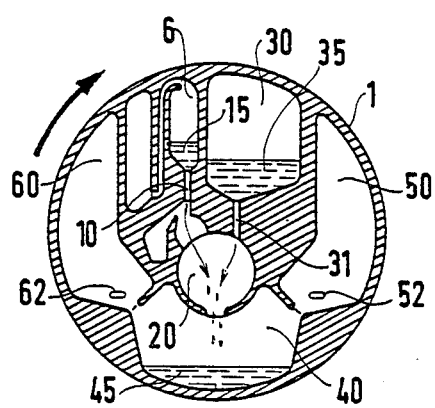

A second centrifugal operation is then performed (see FIGS. 12 and 13). The sample 15 passes through the capillary duct 10 into the pouring chamber 20 and then into the reaction chamber 40. Simultaneously, the diluent 35 passes along the capillary duct 31 into the pouring chamber 20 and into the reaction chamber 40. A first sample-diluent-reagent mixture 45 is thus obtained (see FIG. 13).

As can be seen in FIG. 14, the container is rotated a second time about its own axis, this time through 90°. The direction of the capillary duct 51 is then such that the mixture 45 is expelled into the reaction chamber 50 by a third centrifuging operation (see FIGS. 14 and 15). A new mixture 55 is then obtained in the chamber 50 containing the reagent 52.

The container 1 is again rotated through 90° about its own axis (see FIG. 16) and a fourth centrifuging operation is performed (see FIGS. 16 and 17) to transfer the mixture 55 from the reaction chamber 50 into the reaction chamber 40.

The container 1 is rotated a final time through 90° about its own axis (see FIG. 18) and a fifth centrifuging operation is performed to expel the mixture 55 from the chamber 40 into the chamber 60 where the final mixture 65 is made using the reagent 62, which final mixture may be observed by any suitable means.

The above description relates to the use of a single diluent and three solid reagents. However, some reactions only require one or two solid reagents, in which case some of the reaction chambers may be left empty. Alternatively, several different types of container may be provided having different numbers of reaction chambers.

I claim:

1. A method of performing medical analysis on a liquid sample using at least one dry reagent together with a diluent, using a container having internal compartments including:
    a storage chamber for said liquid sample connected via a capillary duct to one end of a calibrated cell whose other end is connected via a capillary duct to an overflow chamber;
    a storage chamber for said liquid diluent;
    a pouring chamber, a capillary duct connected at one end to said pouring chamber and on the other end to said calibrated cell, a capillary duct connected at one end to said pouring chamber and at the outer end to said diluent storage chamber, and a further capillary duct connected at one end to said pouring chamber and at the other end with a first reaction chamber suitable for containing a dry reagent; and
    two reaction chambers suitable for containing dry reagents situated on either side of said first reaction chamber, and connected via capillary ducts having different angular orientations;
    a lid for closing said container fitted both with a sample storing receptacle connected directly with said sample storage chamber and situated thereabove, and with a removable stopper which penetrates into said pouring chamber to close the ends of said capillary ducts leading thereto; and
    means provided for mounting said container on the turntable of a centrifuge with the axis of the container offset from the axis of the turntable for rotation of the container about said container axis to a plurality of different predetermined positions relative to the turntable and through a given angle to permit selective alignment of a given capillary duct with the direction of centrifuging force resulting from turntable rotation;

said method comprising the steps of:

providing a liquid diluent initially in said diluent storage chamber and dry reagents in respective ones of said reaction chambers;

inserting said sample into the sample storing receptacle and then flowing said sample under gravity into said sample storage chamber, removing said stopper, mounting said container on said centrifuge turntable, operating said turntable and performing a plurality of successive centrifuging operations, while setting the angular position of the container on each occasion from among said predetermined angular positions as a function of the orientation of the capillary duct concerned relative to the direction of centrifugal force in such a manner as to cause said sample to pass successively via said capillary ducts from said sample storage chamber into said calibrated cell, then into said pouring chamber, and then into said first reaction chamber, and subsequently into each of the other reaction chambers.

2. A method according to claim 1, wherein said predetermined positions of the container are separated from one another by rotations of about 90° and about 180°, and correspond substantially to angles between said capillary ducts.

3. Apparatus for performing medical analysis on a liquid sample using at least one dry reagent together with a diluent, said apparatus comprising a single-piece container made of molded plastics material and closed by a single-piece lid made of molded plastics material, said container being compartmented internally to include:

a first storage chamber for said liquid sample connected via a capillary duct to one end of a calibrated cell whose other end is connected via a capillary duct to an overflow chamber;

a storage chamber for said liquid diluent;

a pouring chamber, a capillary duct connected at one end to said pouring chamber and on the other end to said calibrated cell, a capillary duct connected at one end to said pouring chamber and at the outer end to said diluent storage chamber, and a further capillary duct connected at one end to said pouring chamber at the other end with a first reaction chamber suitable for containing a dry reagent; and two reaction chambers suitable for containing dry reagents situated on either side of said first reaction chamber and being connected therewith via capillary ducts having different angular orientations;

said lid being provided both with a sample storing receptacle communicating directly with said sample storage chamber and situated thereabove, and with a chimney situated above said pouring chamber and receiving a stopper suitable for closing off any orifice opening into said pouring chamber.

4. Apparatus according to claim 3, wherein two capillary ducts causing said calibrated cell and said diluent storage chamber to communicate with the pouring chamber extend parallel to each other and the capillary ducts causing the reaction chambers to communicate with one another are diametrically opposed about the pouring chamber and are at a non-zero angle relative to the two said capillary ducts.

5. Apparatus according to claim 3, wherein said container is generally flat and cylindrical having a diameter of about 3 centimeters, and wherein the capillary ducts have a diameter of about 2 tenths of a millimeter.

6. Apparatus according to claim 3, wherein said diluent storage chamber contains a few microliters of diluent and each of said reaction chambers contains a dry reagent in the form of a pencil lead shaped pellet having a length of a few millimeters.

* * * * *